(12) United States Patent
Gracey et al.

(10) Patent No.: US 8,822,748 B2
(45) Date of Patent: Sep. 2, 2014

(54) PROCESS FOR PREPARING ETHENE

(75) Inventors: Benjamin Patrick Gracey, Hull (GB);
Stephen Roy Partington, Beverley (GB)

(73) Assignee: BP P.L.C., London (GB)

( * ) Notice: Subject to any disclaimer, the term of this patent is extended or adjusted under 35 U.S.C. 154(b) by 197 days.

(21) Appl. No.: 12/734,215

(22) PCT Filed: Oct. 8, 2008

(86) PCT No.: PCT/GB2008/003406
§ 371 (c)(1),
(2), (4) Date: Apr. 19, 2010

(87) PCT Pub. No.: WO2009/050433
PCT Pub. Date: Apr. 23, 2009

(65) Prior Publication Data
US 2010/0249481 A1    Sep. 30, 2010

(30) Foreign Application Priority Data

Oct. 17, 2007   (EP) .................................... 07254117

(51) Int. Cl.
*C07C 1/24*    (2006.01)
*C07C 1/20*    (2006.01)

(52) U.S. Cl.
CPC .............. *C07C 1/20* (2013.01); *C07C 2523/30* (2013.01)
USPC ............................ 585/639; 585/638; 585/640

(58) Field of Classification Search
USPC .................. 585/408, 733, 638–642; 560/247; 260/682
See application file for complete search history.

(56) References Cited

U.S. PATENT DOCUMENTS

| | | | |
|---|---|---|---|
| 4,232,179 A | * | 11/1980 | Valladares Barrocas et al. ............................. 585/640 |
| 4,687,875 A | * | 8/1987 | Currie et al. .................. 585/469 |
| 6,187,949 B1 | * | 2/2001 | Froom et al. .................. 560/247 |

FOREIGN PATENT DOCUMENTS

| | | |
|---|---|---|
| EP | 1 792 885 | 6/2007 |
| SU | 127252 A1 | 10/1960 |
| WO | 2007/003899 | 1/2007 |

OTHER PUBLICATIONS

Lee et al, Catalysis of heteropoly compounds. An NMR study of ethanol dehydration in the pseudoliquid phase of 12-tungstophosphoric acid, J. Amer. Chem. Soc. 1992, 114, 2836-2842.*

International Search Report for PCT/GB2008/003406, mailed Dec. 4, 2008.

Written Opinion of the International Searching Authority for PCT/GB2008/003406, mailed Dec. 4, 2008.

International Preliminary Report on Patentability, International Application No. PCT/GB2008/003406, International Filing Date Oct. 8, 2008 (7 pgs).

Office Action issued in Russian Patent Application No. 2010 119 413, English Translation of the Decision to grant dated Jun. 4, 2012 (6 pgs).

* cited by examiner

*Primary Examiner* — In Suk Bullock
*Assistant Examiner* — Sharon Pregler
(74) *Attorney, Agent, or Firm* — Nixon & Vanderhye, P.C.

(57) ABSTRACT

Process for the production of ethene by the vapor phased chemical dehydration of a feed containing ethanol, water and ethoxyethane in a reactor at elevated temperature and pressure in the presence of a bed of catalyst comprising a supported heteropolytungstic acid, by maintaining or configuring the reactor so that it operates in a regime which satisfies the following parameters:

$$0.05 < (P_{water}/P_{ethanol} + P_{ethoxyethane}))/(8 \times 10^{-5} \times GHSV + 0.75) \quad (1)$$

and $$-20 < T_{reaction} - T_{dew\ point} - 40 \times P_{total\ feed} + 40 \times P_{inerts} < +80 \quad (2)$$

wherein $P_{water}$, $P_{ethanol}$ and $P_{ethoxyethane}$, GHSV, $T_{reaction}$, $T_{dew\ point}$, $P_{total\ feed}$ and $P_{inerts}$ are as defined in the specification.

13 Claims, 1 Drawing Sheet

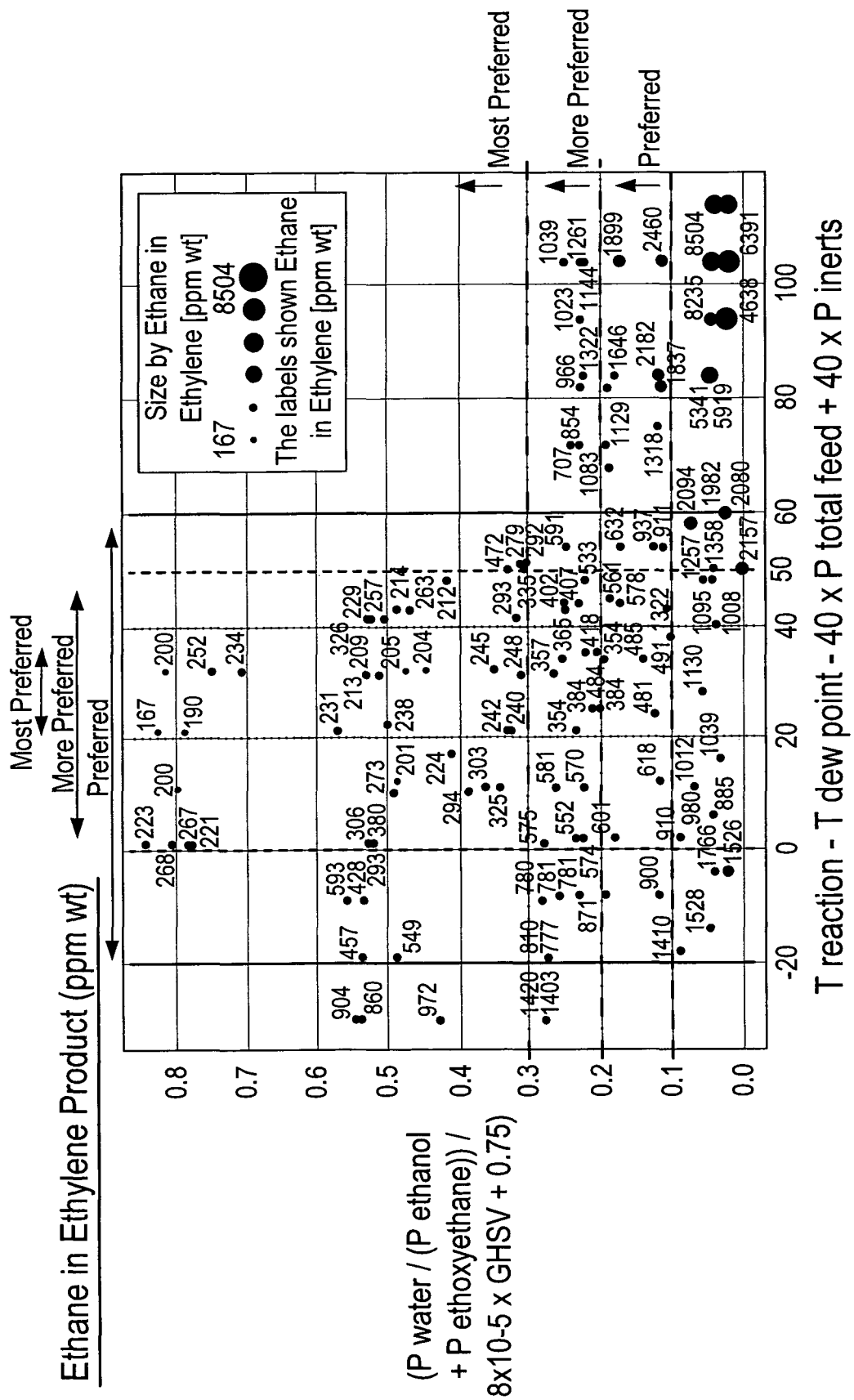

PROCESS FOR PREPARING ETHENE

This application is the U.S. national phase of International Application No. PCT/GB2008/003406, filed 8 Oct. 2008, which designated the U.S. and claims priority to European Application No. 07254117.0, filed 17 Oct. 2007, the entire contents of each of which are hereby incorporated by reference.

The present invention relates to a process for producing ethene by the vapour phase dehydration of ethanol using a heteropolyacid catalyst.

BACKGROUND OF THE INVENTION

Ethene is an important commodity chemical and monomer which has traditionally been produced industrially by the steam or catalytic cracking of hydrocarbons derived from crude oil. However as reserves of crude oil diminish and prices rise there becomes an increasing need to find alternative economically viable methods of making this product. By virtue of its ready availability from the fermentation of biomass and synthesis gas based technologies, ethanol is emerging as an important potential feedstock from which ethene can be made in the future.

The production of ethene by the vapour phase chemical dehydration of ethanol is a well known chemical reaction which has been operated industrially for many years (see for example Kirk Othmer Encyclopaedia of Chemical Technology (third edition), Volume 9, pages 411-413). Traditionally this reaction has been carried out at elevated temperature and low pressure in the presence of an acid catalyst such as activated alumina or supported phosphoric acid.

In recent years attention has turned to finding alternative new catalysts having improved performance. Our co-pending European patent application 06255980.2 discloses such an approach by providing a process involving the use of a supported heteropolyacid catalyst satisfying the relationship:

PV>0.6−0.3×[HPA loading/Surface Area of Catalyst]

wherein PV is the pore volume of the dried supported heteropolyacid catalyst (measured in ml/g catalyst); HPA loading is the amount of heteropolyacid present in the dried supported heteropolyacid catalyst (measured in micro moles/g catalyst) and Surface Area of Catalyst is the surface area of the dried supported heteropolyacid catalyst (measured in $m^2$/g catalyst). The process described in this patent application is carried out at elevated temperature typically between 180 and 250° C. The catalysts described show higher ethene productivity and lower ethane make than those of the prior art. This is desirable because firstly ethane is an undesirable by-product and secondly its separation from ethene on a large scale is both difficult and energy intensive. Our European patent application EP 1792885 and PCT application WO 2007/03899 disclose preferred modes of carrying out the process.

In processes of the type described in this patent application a feed comprising ethanol, optionally water and other components are continuously fed to a reactor containing a bed of heteropolyacid catalyst and the products continuously removed. Under steady state conditions the feed entering the reactor is rapidly converted near the inlet into an equilibrium mixture of water, ethanol and ethoxyethane (the product of a rapid first stage dehydration of the ethanol). The catalyst therefore works in the presence of significant amounts of water the exact amount of which will depend on the equilibrium concentration described above (which itself is dependent upon the overall temperature and pressure of the reactor). In fact the situation is even more complicated because as conversion of the feed occurs in the catalyst bed further water is generated. So depending on the geometry of the reactor the water concentration in the catalyst bed can vary from significant (for example in a tubular fixed bed) to very little (for example in a fluid bed). This variation in water concentration also depends on the temperature of the reactor and the contact time of the feed with the catalyst.

SUMMARY OF THE INVENTION

It has now been found that the amount of water present in processes of the type described in European Patent application 06255980.2 significantly affects the relative amounts of ethene and ethane which the catalyst produces. Controlling the water levels is therefore a very important step in maximising ethene yield and minimising ethane make in processes of this type. The exact mechanism by which water affects these yields is not presently known but one theory suggest that condensation of water in the pores of the catalyst may play an important role. The degree to which this occurs will depend on how close the feed mixture is to its 'dew point' at the operating conditions of the reactor.

The present invention therefore provides a method of operating the reactor in processes of this type so that it is managed or configured so as to operate in a regime where the catalyst bed has an optimum level of catalyst wetness.

According to the present invention there is provided a process for the production of ethene by the vapour phase chemical dehydration of a feed comprising ethanol, water and ethoxyethane in a reactor at elevated temperature and pressure in the presence of a bed of catalyst comprising a supported heteropolytungstic acid characterised in that the reactor is maintained or configured so that it operates in a regime which satisfies the following parameters:

$$0.05 < (P_{water}/P_{ethanol}+P_{ethoxyethane}))/(8\times10^{-5}\times GHSV+ 0.75) \quad (1)$$

and $$-20 < T_{reaction} - T_{dew\ point} - 40\times P_{total\ feed} + 40\times P_{inerts} < +80 \quad (2)$$

wherein $P_{water}$, $P_{ethanol}$ and $P_{ethoxyethane}$ are respectively the partial pressures of water, ethanol and ethoxyethane in the thermodynamic equilibrium composition of the feed at the operating temperature and pressure of the process (in MPa), GHSV is the gas hourly space velocity of feed over the catalyst in $hr^{-1}$, $T_{reaction}$ is the temperature of reaction in ° C., $T_{dew\ point}$ is the dew point temperature of the feed at its thermodynamic equilibrium composition in ° C. at the reaction pressure, $P_{total\ feed}$ is the total pressure of feed (in MPa) and $P_{inerts}$ is the partial pressure of inerts in the feed (in MPa).

It has surprisingly been found that using supported heteropoly acids in an operating regime defined by parameters (1) and (2) above maximises the yield of ethene whilst at the same time minimising ethane selectivity. The process of the present invention also has the additional advantage that the formation of other by-products such as ethanal are likewise minimised.

Parameter (2) above can be considered as providing a measure of the wetness of the catalyst in its working state. It is thought that at reaction temperatures near to the dew point of the particular feed being used (at its thermodynamic equilibrium composition) the catalyst is too wet and unacceptably high levels of ethane are produced (typically in excess of 600 ppm in the ethene product). A similar effect also occurs when the reaction temperature is significantly in excess of the dew point of the feed (at its thermodynamic equilibrium composition) when the catalyst is effectively too dry. Only when the difference between the reaction temperature and the dew point of the feed (at its thermodynamic equilibrium composition and allowing for the amount of inerts present) is sufficient to bring it within the parameter disclosed above are very low levels of ethane, typically less than 600 ppm preferably below 250 ppm, obtained.

Parameter (1) above provides a measure of the overall wetness of the process. It has been found that when the water content of the feed is relatively speaking high the amount of ethane produced is again low. This reduction is further improved if the gas hourly space velocity is lowered by virtue of the fact that there is higher conversion of the feed to ethene. This phenomenon is optimised when parameter (1) is satisfied.

As regards the operating conditions of the process, the temperature of reaction should be in the range 180 to 270° C. preferably 200 to 250° C., most preferably 210 to 240° C. and the total reaction pressure in the range 1 to 3 MPa To realise the improvements described herein it is preferable to choose operating conditions such that the amount of ethane contained in the reactor effluent is at least less than 1000 ppm preferably less than 600 ppm most preferably less than 250 ppm. In order to achieve these low levels of ethane it is preferred that the operating conditions are such that for parameter (1):

$$0.1 < (P_{water}/P_{ethanol}+P_{ethoxyethane}))/(8\times10^{-5}\times GHSV+0.75)$$

more preferably:

$$0.2 < (P_{water}/P_{ethanol}+P_{ethoxyethane}))/(8\times10^{-5}\times GHSV+0.75)$$

and most preferably:

$$0.3 < (P_{water}/P_{ethanol}+P_{ethoxyethane}))/(8\times10^{-5}\times GHSV+0.75)$$

and for parameter (2):

$$-20 < T_{reaction} - T_{dew\ point} - 40\times P_{total\ feed} + 40\times P_{inerts} < 60$$

more preferably:

$$0 < T_{reaction} - T_{dew\ point} - 40\times P_{total\ feed} + 40\times P_{inerts} < 50.$$

and most preferably:

$$20 < T_{reaction} - T_{dew\ point} - 40\times P_{total\ feed} + 40\times P_{inerts} < 40$$

BRIEF DESCRIPTION OF THE DRAWINGS

The invention is further described with reference to the accompanying drawing, in which FIG. 1 is a plot of $(P_{water}/(P_{ethanol}+P_{ethoxyethane}))/(8\times10^{-5}\times GHSV+0.75)$ versus $T_{reaction}-T_{dew\ point}-40\times P_{total\ feed}+40\times P_{inerts}$ It will be appreciated that any combination of the preferred ranges of these two parameters are able to provide a benefit and are contemplated by the invention disclosed herein. This is further illustrated by FIG. 1.

As mentioned above, when operating within the regime defined by parameters (1) and (2), the feed in the reactor contents will be at equilibrium and will comprise from 0 to 65% by volume ethoxyethane, from 0 to 15% by volume water and from 0 to 20% by volume ethene. The gas hourly space velocity (GHSV) will typically be in the range 500 to 10000 hr$^{-1}$. Preferably the GHSV is in the range 1000 to 5000 and most preferably the GHSV is in the range 2000 to 4000, The equilibrium feed composition can either be created in the front end of the reactor or in a precursor etherification reactor. The latter approach allows the exotherm associated with the first stage etherification process to be managed thereby avoiding localised 'hotspots' in the bed. It is also preferred if the ethanol is derived from biomass sources as this will in general contain significant amounts of water which needs to be removed before being fed to the reactor. In such circumstances a reactive distillation column for combined etherification and water separation can be used to great advantage. Alternatively the etherification and separation stages can be operated separately and easily given the low boiling point of ethoxyethane relative to water and the low propensity of these two components to form azeotropes.

In an embodiment of the invention it is preferred to use an inert, non-condensable diluent in the feed to control the degree of catalyst wetness and to attain the regime defined in parameter (2). Preferred diluents are nitrogen, helium, ethene, saturated hydrocarbons which are gaseous under the reaction conditions, with 2-methylpropane, n-butane and ethene being most preferred. It is preferred that the levels of inert diluent used are such that the value of parameter (2) lies in the range 25 to 30. Use of said diluent allows, for a given total reactor pressure, a higher ethene productivity and a lower ethane by-product make. Adjustment of the amount of diluent can be important for optimising catalyst lifetime within the reactor. The use of a diluent with a boiling intermediate between ethanal and ethene on the one hand or ethoxyethane and ethene on the other is desirable in order to facilitate downstream separation of ethene from these other components. Using this approach ethene containing less than 10 ppm of oxygen containing compound can be produced. The diluent can be advantageously added down the catalyst bed or between a series of catalyst beds (if so used) in order to maintain the operating regime of the invention. Finally using diluents facilitates the use of feeds containing a higher level of water than mentioned above (typically greater than 15% by volume in the equilibrium composition, preferably 20% by volume or above).

The term heteropolytungstic acid as used herein includes both the free acids themselves and derivatives thereof. Said derivatives include inter alia; alkali, alkali earth; ammonium, free acids, bulky cation salts, and/or metal salts (where the salts may be either full or partial salts) of heteropolytungstic acids. Hence, the heteropolytungstic acids used in the present invention are complex, high molecular weight anions comprising oxygen-linked metal atoms.

Typically, each anion comprises 12-18, oxygen-linked tungsten atoms. These atoms surround one or more of central atoms in a symmetrical manner. The central atoms are preferably silicon or phosphorus, but may alternatively comprise any one of a large variety of atoms from Groups I-VIII in the Periodic Table of elements. These include copper, beryllium, zinc, cobalt, nickel, boron, aluminium, gallium, iron, cerium, arsenic, antimony, bismuth, chromium, rhodium, silicon, germanium, tin, titanium, zirconium, vanadium, sulphur, tellurium, manganese nickel, platinum, thorium, hafnium, cerium, arsenic, vanadium, antimony ions, tellurium and iodine. Suitable heteropolytungstic acids include Keggin, Wells-Dawson and Anderson-Evans-Perloff heteropolytungstic acids. Specific examples of suitable heteropolytungstic acids are as follows:

18-tungstophosphoric acid—$H_6[P_2W_{18}O_{62}].xH_2O$
12-tungstophosphoric acid—$H_3[PW_{12}O_{40}].xH_2O$
12-tungstosilicic acid—$H_4[SiW_{12}O_{40}].xH_2O$ Cesium hydrogen tungstosilicate—Cs3H[SiW12 O40].xH2O and the free acid or partial salts of the following heteropolytungstic acids:

Monopotassium tungstophosphate—KH5[P2W18 O62].xH2O

Monosodium 12-tungstosilicic acid—NaK3 [SiW12 O40].xH2O

Potassium tungstophosphate—K6[P2W18O62].xH2O

In addition mixtures of different heteropolytungstic acids and salts can be employed. The preferred ones for use in the process described by the present invention are any those based on the Keggin or Wells-Dawson structures; more preferably the chosen heteropolytungstic acid for use in the process described by the present invention is either: tungstosilicic acid, or tungstophosphoric acid. Most preferably the heteropolytungstic acid is 12-tungstosilicic acid ($H_4[SiW_{12}O_{40}].xH_2O$).

Preferably, the heteropolytungstic acids employed according to the present invention have molecular weights of more than 700 and less than 8500, preferably more than 2800 and less than 6000. Such heteropolytungstic acids also include dimeric complexes.

The supported heteropolytungstic acid catalyst may be conveniently prepared by dissolving the chosen heteropolytungstic acid in a suitable solvent, where suitable solvents include polar solvents such as water, ethers, alcohols, carboxylic acids, ketones and aldehydes and/or mixtures thereof and distilled water and/or ethanol are the most preferred solvents. The resulting acidic solution has a heteropolytungstic acid concentration that is preferably comprised between 10 to 80 wt %, more preferably 20 to 70 wt % and most preferably 30 to 60 wt %. This said solution is then added to the chosen support (or alternatively the support is immersed in the solution). The actual volume of acidic solution added to the support is not restricted, and hence may be enough to achieve incipient wetness or wet impregnation, where wet impregnation (i.e. preparation using an excess acidic solution volume relative to pore volume of support), is the preferred method for the purposes of the present invention.

The resulting supported heteropolytungstic acid may be modified, and various salts of heteropolytungstic acid may then be formed in the aqueous solution either prior to, or during, impregnation of the acidic solution onto the support, by subjecting the supported heteropolytungstic acid to a prolonged contact with a solution of a suitable metallic salt or by addition of phosphoric acid and/or other mineral acids.

When using a soluble metallic salt to modify the support, the salt is taken in the desired concentration, with the heteropolytungstic acid solution. The support is then left to soak in the said acidic solution for a suitable duration (e.g. a few hours), with periodic stirring or shaking, after which time it is filtered, using suitable means, in order to remove any excess acid.

When the salt is insoluble it is preferred to impregnate the catalyst with the heteropolytungstic acid and then to titrate with the salt precursor. This method can improve the dispersion of the heteropolytungstic acid salt. Other techniques such as vacuum impregnation may also be employed.

The impregnated support may then be washed and dried. This may be achieved using any conventional separation technique, including, for example, decantation and/or filtration. Once recovered, the impregnated support may be dried, preferably by placing the support in an oven at elevated temperature. Alternatively, or additionally, a dessicator may be employed. On a commercial scale this drying stage is often achieved by a purge of hot inert gas such as nitrogen.

A preferred heteropolytungstic acid supported catalyst is one having the following characteristic:

$$PV > 0.6 - 0.3 \times [HPA\ loading/Surface\ Area\ of\ Catalyst]$$

wherein PV is the pore volume of the dried supported heteropolytungstic acid catalyst (measured in ml/g catalyst); HPA loading is the amount of heteropolyacid present in the dried supported heteropolyacid catalyst (measured in micro moles per gram of catalyst) and Surface Area of Catalyst is the surface area of the dried supported heteropolytungstic acid catalyst (measured in $m^2$ per gram of catalyst).

The amount of heteropolytungstic acid impregnated onto the support is suitably in the range of 10 wt % to 80 wt % and preferably in between 20 wt % to 50 wt %, based on the total weight of the heteropolytungstic acid and of the support.

The weight of the catalyst on drying and the weight of the support used, may be used to obtain the weight of the acid on the support by deducting the latter from the former, giving the catalyst loading as a 'g heteropolytungstic acid/kg catalyst' term. The catalyst loading in 'grams of heteropolytungstic acid/liter support' can also be calculated by using the known or measured bulk density, of the support. The preferred catalytic loading of heteropolytungstic acid is 150 to 600 g heteropolytungstic acid/kg catalyst According to a preferred embodiment of the present invention the average heteropolytungstic acid loading per surface area of the dried supported heteropolytungstic acid catalyst is more than 0.1 micro moles/$m^2$.

It should be noted that the polyvalent oxidation states and hydration states of the heteropolytungstic acids stated previously, and as represented in the typical formulae of some specific compounds (shown above), only apply to the fresh acid before it is impregnated onto the support, and especially before it is subjected to the dehydration process conditions of the present invention. The degree of hydration of the heteropolytungstic acid may affect the acidity of the supported catalyst and hence its activity and selectivity. Thus, either or both of these actions of impregnation and dehydration process may change the hydration and oxidation state of the metals in the heteropolytungstic acids, i.e. the actual catalytic species used, under the process conditions given, may not yield the hydration/oxidation states of the metals in the heteropolytungstic acids used to impregnate the support. Naturally therefore it is only to be expected that such hydration and oxidation states may also be different in the spent catalysts after the dehydration process of the present invention.

According to a preferred embodiment of the present invention, the amount of chloride present in/on the said heteropolytungstic acid supported catalyst is less than 40 ppm, preferably less than 25 ppm and most preferably less than 20 ppm.

Suitable catalyst supports may be in a powder form or alternatively may be in a granular form, or in a pelletised form, a spherical form or as a extrudates (including shaped particles) and include, but are not limited to, Mordenites e.g. montmorillonite, clays, bentonite, diatomous earth, titania, activated carbon, alumina, silica-alumina, silica-titania cogels, silica-zirconia cogels, carbon coated alumina, zeolites, zinc oxide, flame pyrolysed oxides. Supports can be mixed oxides, neutral or weakly basic oxides. Silica supports are preferred, such as silica gel supports and supports produced by the flame hydrolysis of $SiCl_4$. Preferred supports are substantially free of extraneous metals or elements which might adversely affect the catalytic activity of the system. Thus, suitable silica supports are at least 99% w/w pure. Impurities amount to less than 1% w/w, preferably less than 0.60% w/w and most preferably less than 0.30% w/w. The pore volume of the support is preferably more than 0.50 ml/g and preferably more than 0.8 ml/g.

Suitable silica supports include, but are not limited to any of the following: Grace Davison Davicat® Grade 57, Grace Davison Davicat® 1252, Grace Davison Davicat® SI 1254, Fuji Silysia CariAct® Q15, Fuji Silysia CariAct® Q10, Degussa Aerolyst® 3045 and Degussa Aerolyst® 3043. The average diameter of the support particles is 2 to 10 mm, preferably 3 to 6 mm. However, these particles may be crushed and sieved to smaller sizes of, for example, 0.5-2 mm, if desired.

The average pore radius (prior to impregnation with the heteropolytungstic acid) of the support is 10 to 500 Å, preferably 30 to 175 Å, more preferably 50 to 150 Å and most preferably 60 to 120 Å. The BET surface area is preferably between 50 and 600 m2/g and is most preferably between 150 and 400 m2/g. The support has an average single particle crush strength of at least 1 kg force, suitably at least 2 kg force, preferably at least 6 kg force and more preferably at least 7 kg force. The bulk density of the support is at least 380 g/l, preferably at least 395 g/l.

The single particle crush strength was determined by using a Mecmesin force gauge which measures the minimum force necessary to crush a particle between parallel plates. The crush strength is based on the average of that determined for a set of at least 25 catalyst particles.

The BET surface area, pore volume, pore size distribution and average pore radius were determined from the nitrogen adsorption isotherm determined at 77K using a Micromeritics TRISTAR 3000 static volumetric adsorption analyser. The procedure used was an application of British Standard methods BS4359:Part 1:1984 'Recommendations for gas adsorption (BET) methods' and BS7591:Part 2:1992, 'Porosity and pore size distribution of materials'—Method of evaluation by gas adsorption. The resulting data were reduced using the BET method (over the pressure range 0.05-0.20 P/Po) and the Barrett, Joyner & Halenda (BJH) method (for pore diameters of 20-1000 Å) to yield the surface area and pore size distribution respectively.

Suitable references for the above data reduction methods are Brunauer, S, Emmett, P H, & Teller, E, J. Amer. Chem. Soc. 60, 309, (1938) and Barrett, E P, Joyner, L G & Halenda P P, J. Am Chem. Soc., 1951 73 373-380.

Samples of the supports and catalysts were out gassed for 16 hours at 120° C. under a vacuum of 5×10-3 Torr prior to analysis.

In a preferred aspect further the chosen catalyst support is first treated with a fluorinating agent; the applicants believe that by fulfilling this said embodiment the catalyst will become more inert and/or acidic thus improving the selectivity and/or effectiveness of the catalyst during the aforementioned dehydration process.

Numerous approaches can be taken to ensuring that the reactor is operated or maintained in the regime disclosed above. It should be recognised at the outset that the process of the present invention is overall endothermic therefore an important issue in remaining within the process window defined by parameters (1) and (2) above is the need to input heat into the reactor. In one embodiment therefore the reaction is effected in a series of two or more reactors operated adiabatically in which conversion of the feed is progressive and the each subsequent reactor is operated at a higher temperature than the previous one. Alternatively if a single reactor is used heating can be supplied at various intervals along the bed to create an increasing temperature gradient thereby maintaining catalyst activity and selectivity. With knowledge of the above mentioned regime the optimum temperatures and hence optimum heating requirements can be calculated and used. In this case the use of water removal and recycle of product streams can be used to advantage.

In a second embodiment which can be used on a stand alone basis or combined with embodiment the shape or configuration of the reactor can be changed to change the catalyst feed contact time. For example a reactor configured so that its cross-sectional area progressively increases along the bed can be employed. Alternatively a radial design can be envisaged where the feed flows out from a central location though cylinders of progressively increasing diameter and therefore active surface area.

In yet another embodiment the contact time between the heteroployacid and the feed can be increased by using a progressively less diluted catalyst down the bed (either by mixing with a diluent or using a catalyst with a progressively higher heteropolytungstic acid loading. Such an approach allows better management of the catalyst and front-end exotherms created by the initial equilibration of the feed referred to above.

It is believed that the principles disclosed above will be applicable to the chemical dehydration of 2-methyl propan-1-ol, 2-methyl propan-2-ol, n-propanol, propan-2-ol.

The present invention is now illustrated by reference to the following examples.

Support Materials Used in the Examples

Silica pellets of CariAct® Q15 were obtained from Fuji Silysia

Silica extrudates of Aerolyst® 3045 were obtained as extrudates from Degussa

Silica granules of Davicat® Grade 57 were obtained from Grace Davison.

Support Properties

The support materials were analysed by nitrogen porosimetry.

| Support | Surface Area (m2/g) | Pore Volume (cm3/g) | Mean PSD (Å) |
|---|---|---|---|
| Aerolyst 3045 | 156 | 0.93 | 239 |
| CariAct Q15 | 208 | 1.02 | 196 |
| Davicat Grade 57 | 284 | 1.11 | 156 |

Catalyst Preparations Using Water as Solvent

Silicotungstic acid (H4[SiW12O40].24H2O, Mw 3310.6) was weighed into a wide-necked plastic bottle and dissolved in distilled water. To this acid solution was added a weighed amount of the support material. The acid solution and support material was left to soak for approxiniately 1 hr with the occasional gentle swirl during this period to dislodge any trapped air bubbles.

After soaking the unadsorbed acid solution was removed by pouring the acid solution and support material out of the plastic container and into a plastic filter (which contained a filter paper).

The catalyst was allowed to drain until for approximately 15 to 60 minutes until no more liquid was being removed from the catalyst.

After draining was complete the catalyst was transferred to a ceramic tray and dried in a muffle furnace at 130° C. under nitrogen.

The dried solid catalyst was weighed and the amount of silicotungstic acid adsorbed on the catalyst calculated by difference in weight to the starting material as indicated in the following table.

| Catalyst | Support | Support wt (g) | HPA (g) | Water for HPA solution (g) | Weight catalyst g | HPA absorbed (g) | HPA Loading g/kg |
|---|---|---|---|---|---|---|---|
| A | CariAct Q15 | 200.00 | 200.08 | 453.77 | 270.78 | 70.78 | 261 |
| B | Aerolyst 3045 | 30.03 | 28.37 | 64.14 | 40.94 | 10.91 | 266 |
| C | G57 | 30.06 | 32.34 | 76.68 | 41.83 | 11.77 | 281 |

Catalyst Properties
The dried solid catalysts were analysed by nitrogen porosimetry:

| Catalyst | Support | Surface Area of Catalyst (m2/g) | Pore Volume of Catalyst (cm3/g Cat) | Mean PSD of Catalyst (Å) | HPA (g)/ Surface Area of Catalyst (m2) | HPA (μmoles)/ Surface Area of Catalyst (m2) | Calculation of Equation (3) |
|---|---|---|---|---|---|---|---|
| A | CariAct Q15 | 160 | 0.71 | 177 | 0.00163 | 0.492 | 0.4520 |
| B | Aerolyst 3045 | 119 | 0.63 | 212 | 0.00224 | 0.677 | 0.400 |
| C | G57 | 239 | 0.69 | 116 | 0.00118 | 0.356 | 0.493 |

Equation (3)=0.6−0.3[HPA Loading (umoles/g)/ Surface Area of Catalyst (m2/g)]

When calculating the micromoles of heteropolyacid (HPA) adsorbed on the catalyst it is assumed that the hetropolyacid is fully hydrated. A Mw of 3310.6 was used for calculating the micro moles of 12-silicotungstic acid ($H_4[SiW_{12}O_{40}] \cdot 24H_2O$) adsorbed Catalyst Testing
Catalysts (125 to 180 μm diameter particle size) were loaded into parallel flow reactors. Volumes of the catalysts in the parallel reactors ranged from 0.083 to 0.97 mls. The reactors were pressure tested and then heated to 220° C. under a nitrogen flow. When the temperature had reached 220° C. the liquid feed of ethanol, ethoxyethane and water were vapourised and mixed with nitrogen prior to being admitted to the reactor containing the catalyst. The reaction conditions were 2.0 MPa, EtOH (28% v/v), ethoxyethane (34.5% v/v), water (3.3% v/v), nitrogen (32.7% v/v) and methane (1.5% v/v, used as an internal standard since this compound is not formed to any significant degree during the dehydration process). A constant gas flow to each reactor allowed GHSV to be varied according to the catalyst volume loaded. The catalysts were tested under these conditions for 100 hrs before feed compositions, pressures and temperatures were varied. Gas chromatography of the product stream was used to measure the yields of ethane and ethene (using nitrogen gas as an internal standard.

Calculation of Dew Point
The calculation of the dew point of the feed at its equilibrium composition was made using an AspenPlus RGIBBS reaction block, with fluid mixture physical properties predicted using Predictive Soave Redlich Kwong (PSRK)

EXAMPLES

| Ex | Catalyst | N2 Feed (mol %) | EtOH Feed (mol %) | Ethoxyethane Feed (mol %) | Water Feed (mol %) | Methane Feed (mol %) | Reactor Temperature (° C.) | Pressure (MPa) | GHSV (h−1) | Dew Point After Reaction to Equilibrium (° C.) | T reaction − T dew point − 40 × P total feed + 40 × P inerts | (P water/ (P ethanol + P ethoxyethane))/ (8 × 10 − 5 × GHSV + 0.75) | Ethene STY (g-l-hr) | Ethane in Ethene (ppm wt) |
|---|---|---|---|---|---|---|---|---|---|---|---|---|---|---|
| 1* | Aerolyst 3045 | 0.327 | 0.5 | 0.125 | 0.033 | 0.015 | 210 | 3.0 | 16700 | 161 | −30 | 0.278 | 116 | 1420 |
| 2* | CariAct Q15 | 0.327 | 0.5 | 0.125 | 0.033 | 0.015 | 210 | 3.0 | 16700 | 161 | −30 | 0.278 | 118 | 1403 |
| 3* | G57 | 0.327 | 0.5 | 0.125 | 0.033 | 0.015 | 210 | 3.0 | 16700 | 161 | −30 | 0.278 | 117 | 1570 |
| 4* | CariAct Q15 | 0.327 | 0.5 | 0.125 | 0.033 | 0.015 | 210 | 3.0 | 7500 | 161 | −30 | 0.429 | 94 | 972 |
| 5* | CariAct Q15 | 0.327 | 0.5 | 0.125 | 0.033 | 0.015 | 210 | 3.0 | 4100 | 161 | −30 | 0.538 | 82 | 904 |
| 6* | Aerolyst 3045 | 0.327 | 0.5 | 0.125 | 0.033 | 0.015 | 210 | 3.0 | 4000 | 161 | −30 | 0.542 | 80 | 860 |
| 7* | G57 | 0.327 | 0.5 | 0.125 | 0.033 | 0.015 | 210 | 3.0 | 3900 | 161 | −30 | 0.546 | 95 | 588 |
| 8 | Aerolyst 3045 | 0.327 | 0.5 | 0.125 | 0.033 | 0.015 | 220 | 3.0 | 16700 | 161 | −19 | 0.275 | 409 | 810 |
| 9 | G57 | 0.327 | 0.5 | 0.125 | 0.033 | 0.015 | 220 | 3.0 | 16700 | 161 | −19 | 0.275 | 411 | 777 |

-continued

| Ex | Catalyst | N2 Feed (mol %) | EtOH Feed (mol %) | Ethoxy ethane Feed (mol %) | Water Feed (mol %) | Methane Feed (mol %) | Reactor Temperature (° C.) | Pressure (MPa) | GHSV (h−1) | Dew Point After Reaction to Equilibrium (° C.) | T reaction − T dew point − 40 × P total feed + 40 × P inerts | (P water/ (P ethanol + P ethoxyethane))/ (8 × 10 − 5 × GHSV + 0.75) | Ethene STY (g-l-hr) | Ethane in Ethene (ppm wt) |
|---|---|---|---|---|---|---|---|---|---|---|---|---|---|---|
| 10 | CariAct Q15 | 0.327 | 0.5 | 0.125 | 0.033 | 0.015 | 220 | 3.0 | 5300 | 161 | −19 | 0.488 | 324 | 549 |
| 11 | Aerolyst 3045 | 0.327 | 0.5 | 0.125 | 0.033 | 0.015 | 220 | 3.0 | 4000 | 161 | −19 | 0.535 | 269 | 457 |
| 12 | Aerolyst 3045 | 0.327 | 0.28 | 0.345 | 0.033 | 0.015 | 210 | 3.0 | 27000 | 154 | −18 | 0.090 | 296 | 1410 |
| 13* | G57 | 0.327 | 0 | 0.608 | 0.05 | 0.015 | 210 | 3.0 | 3900 | 145 | −14 | 0.046 | 548 | 1528 |
| 14 | CariAct Q15 | 0.327 | 0.5 | 0.125 | 0.033 | 0.015 | 230 | 3.0 | 15500 | 160 | −9 | 0.284 | 562 | 790 |
| 15 | G57 | 0.327 | 0.5 | 0.125 | 0.033 | 0.015 | 230 | 3.0 | 3900 | 160 | −9 | 0.533 | 633 | 428 |
| 16 | CariAct Q15 | 0.327 | 0.5 | 0.125 | 0.033 | 0.015 | 230 | 3.0 | 3300 | 160 | −9 | 0.558 | 487 | 593 |
| 17 | G57 | 0.327 | 0.28 | 0.345 | 0.033 | 0.015 | 220 | 3.0 | 18100 | 149 | −8 | 0.118 | 650 | 900 |
| 18 | CariAct Q15 | 0.327 | 0.28 | 0.345 | 0.033 | 0.015 | 220 | 3.0 | 7000 | 149 | −8 | 0.197 | 458 | 871 |
| 19 | Aerolyst 3045 | 0.327 | 0.28 | 0.345 | 0.033 | 0.015 | 220 | 3.0 | 4500 | 149 | −8 | 0.233 | 674 | 781 |
| 20 | CariAct Q15 | 0.327 | 0.28 | 0.345 | 0.033 | 0.015 | 220 | 3.0 | 3100 | 149 | −8 | 0.259 | 396 | 781 |
| 21* | Aerolyst 3045 | 0.327 | 0 | 0.608 | 0.05 | 0.015 | 220 | 3.0 | 16700 | 145 | −4 | 0.023 | 1246 | 1766 |
| 22* | CariAct Q15 | 0.327 | 0 | 0.608 | 0.05 | 0.015 | 220 | 3.0 | 5300 | 145 | −4 | 0.040 | 1036 | 1526 |
| 23 | CariAct Q15 | 0.327 | 0.5 | 0.125 | 0.033 | 0.015 | 240 | 3.0 | 15500 | 160 | 1 | 0.281 | 1134 | 575 |
| 24 | Aerolyst 3045 | 0.327 | 0.5 | 0.125 | 0.033 | 0.015 | 240 | 3.0 | 4000 | 160 | 1 | 0.522 | 860 | 306 |
| 25 | G57 | 0.327 | 0.5 | 0.125 | 0.033 | 0.015 | 240 | 3.0 | 3900 | 160 | 1 | 0.526 | 1126 | 380 |
| 26 | CariAct Q15 | 0.327 | 0.5 | 0.125 | 0.033 | 0.015 | 240 | 3.0 | 3900 | 160 | 1 | 0.526 | 1035 | 293 |
| 27 | Aerolyst 3045 | 0.327 | 0.625 | 0 | 0.033 | 0.015 | 210 | 2.0 | 4500 | 156 | 1 | 0.774 | 148 | 267 |
| 28 | CariAct Q15 | 0.327 | 0.625 | 0 | 0.033 | 0.015 | 210 | 2.0 | 4400 | 156 | 1 | 0.780 | 193 | 221 |
| 29 | G57 | 0.327 | 0.625 | 0 | 0.033 | 0.015 | 210 | 2.0 | 4000 | 156 | 1 | 0.803 | 195 | 223 |
| 30 | CariAct Q15 | 0.327 | 0.625 | 0 | 0.033 | 0.015 | 210 | 2.0 | 3400 | 156 | 1 | 0.841 | 137 | 268 |
| 31 | Aerolyst 3045 | 0.327 | 0.28 | 0.345 | 0.033 | 0.015 | 210 | 2.5 | 27000 | 142 | 2 | 0.090 | 493 | 910 |
| 32 | CariAct Q15 | 0.327 | 0.28 | 0.345 | 0.033 | 0.015 | 210 | 2.5 | 8700 | 142 | 2 | 0.182 | 469 | 591 |
| 33 | CariAct Q15 | 0.327 | 0.28 | 0.345 | 0.033 | 0.015 | 210 | 2.5 | 5200 | 142 | 2 | 0.226 | 466 | 552 |
| 34 | G57 | 0.327 | 0.28 | 0.345 | 0.033 | 0.015 | 210 | 2.5 | 4600 | 142 | 2 | 0.235 | 412 | 574 |
| 35* | Aerolyst 3045 | 0.327 | 0 | 0.608 | 0.05 | 0.015 | 230 | 3.0 | 4000 | 145 | 6 | 0.043 | 1472 | 980 |
| 36* | G57 | 0.327 | 0 | 0.608 | 0.05 | 0.015 | 230 | 3.0 | 3900 | 145 | 6 | 0.044 | 1724 | 885 |
| 37 | CariAct Q15 | 0.327 | 0.5 | 0.125 | 0.033 | 0.015 | 210 | 2.0 | 9400 | 147 | 10 | 0.387 | 280 | 294 |
| 38 | CariAct Q15 | 0.327 | 0.5 | 0.125 | 0.033 | 0.015 | 210 | 2.0 | 5400 | 147 | 10 | 0.492 | 152 | 273 |
| 39 | CariAct Q15 | 0.327 | 0.28 | 0.345 | 0.033 | 0.015 | 210 | 2.3 | 3100 | 139 | 11 | 0.264 | 275 | 581 |
| 40 | Aerolyst 3045 | 0.327 | 0.625 | 0 | 0.033 | 0.015 | 220 | 2.0 | 21600 | 156 | 11 | 0.343 | 810 | 303 |
| 41 | G57 | 0.327 | 0.625 | 0 | 0.033 | 0.015 | 220 | 2.0 | 19700 | 156 | 11 | 0.365 | 745 | 325 |
| 42 | G57 | 0.327 | 0.625 | 0 | 0.033 | 0.015 | 220 | 2.0 | 4000 | 156 | 11 | 0.794 | 439 | 200 |
| 43 | CariAct Q15 | 0.327 | 0.28 | 0.345 | 0.033 | 0.015 | 240 | 3.0 | 36100 | 150 | 11 | 0.069 | 2579 | 1012 |
| 44 | Aerolyst 3045 | 0.327 | 0.28 | 0.345 | 0.033 | 0.015 | 240 | 3.0 | 4500 | 150 | 11 | 0.226 | 1912 | 570 |
| 45 | Aerolyst 3045 | 0.327 | 0.2231 | 0.2749 | 0.16 | 0.015 | 210 | 2.0 | 4500 | 145 | 12 | 0.487 | 185 | 201 |
| 46 | G57 | 0.327 | 0.28 | 0.345 | 0.033 | 0.015 | 220 | 2.5 | 18100 | 142 | 12 | 0.118 | 889 | 618 |
| 47* | CariAct Q15 | 0.327 | 0 | 0.608 | 0.05 | 0.015 | 240 | 3.0 | 7500 | 145 | 16 | 0.033 | 2961 | 1039 |
| 48 | G57 | 0.327 | 0.241 | 0.297 | 0.12 | 0.015 | 210 | 2.0 | 4000 | 140 | 17 | 0.411 | 285 | 224 |
| 49 | CariAct Q15 | 0.3261 | 0.2598 | 0.3191 | 0.08 | 0.015 | 210 | 2.0 | 9400 | 136 | 21 | 0.235 | 351 | 354 |

-continued

| Ex | Catalyst | N2 Feed (mol %) | EtOH Feed (mol %) | Ethoxy ethane Feed (mol %) | Water Feed (mol %) | Methane Feed (mol %) | Reactor Temperature (°C.) | Pressure (MPa) | GHSV (h−1) | Dew Point After Reaction to Equilibrium (°C.) | T reaction − T dew point − 40 × P total feed + 40 × P inerts (°C.) | (P water/ (P ethanol + P ethoxyethane))/ (8 × 10 − 5 × GHSV + 0.75) | Ethene STY (g-l-hr) | Ethane in Ethene (ppm wt) |
|---|---|---|---|---|---|---|---|---|---|---|---|---|---|---|
| 50 | G57 | 0.3261 | 0.2598 | 0.3191 | 0.08 | 0.015 | 210 | 2.0 | 4000 | 136 | 21 | 0.329 | 347 | 242 |
| 51 | CariAct Q15 | 0.3261 | 0.2598 | 0.3191 | 0.08 | 0.015 | 210 | 2.0 | 3900 | 136 | 21 | 0.332 | 315 | 240 |
| 52 | CariAct Q15 | 0.327 | 0.625 | 0 | 0.033 | 0.015 | 230 | 2.0 | 9000 | 156 | 21 | 0.571 | 1253 | 231 |
| 53 | G57 | 0.327 | 0.625 | 0 | 0.033 | 0.015 | 230 | 2.0 | 4000 | 156 | 21 | 0.785 | 788 | 190 |
| 54 | CariAct Q15 | 0.327 | 0.625 | 0 | 0.033 | 0.015 | 230 | 2.0 | 3400 | 156 | 21 | 0.822 | 618 | 167 |
| 55 | G57 | 0.327 | 0.2231 | 0.2749 | 0.16 | 0.015 | 220 | 2.0 | 4000 | 145 | 22 | 0.499 | 473 | 238 |
| 56 | G57 | 0.327 | 0.28 | 0.345 | 0.033 | 0.015 | 210 | 2.0 | 16700 | 134 | 24 | 0.126 | 555 | 481 |
| 57 | G57 | 0.327 | 0 | 0.508 | 0.15 | 0.015 | 210 | 2.0 | 3900 | 132 | 25 | 0.202 | 425 | 384 |
| 58 | CariAct Q15 | 0.327 | 0 | 0.508 | 0.15 | 0.015 | 210 | 2.0 | 3200 | 132 | 25 | 0.213 | 311 | 364 |
| 59 | G57 | 0.327 | 0.125 | 0.5 | 0.033 | 0.015 | 210 | 2.0 | 15500 | 129 | 28 | 0.058 | 641 | 1130 |
| 60 | Aerolyst 3045 | 0.327 | 0.5 | 0.125 | 0.033 | 0.015 | 230 | 2.0 | 4500 | 147 | 31 | 0.512 | 881 | 209 |
| 61 | G57 | 0.327 | 0.5 | 0.125 | 0.033 | 0.015 | 230 | 2.0 | 4000 | 147 | 31 | 0.531 | 977 | 213 |
| 62 | Aerolyst 3045 | 0.3261 | 0.2598 | 0.3191 | 0.08 | 0.015 | 220 | 2.0 | 4500 | 137 | 31 | 0.313 | 598 | 248 |
| 63 | CariAct Q15 | 0.327 | 0.625 | 0 | 0.033 | 0.015 | 240 | 2.0 | 5300 | 156 | 32 | 0.707 | 1190 | 234 |
| 64 | Aerolyst 3045 | 0.327 | 0.625 | 0 | 0.033 | 0.015 | 240 | 2.0 | 4500 | 156 | 32 | 0.748 | 1211 | 252 |
| 65 | CariAct Q15 | 0.327 | 0.625 | 0 | 0.033 | 0.015 | 240 | 2.0 | 3400 | 156 | 32 | 0.812 | 1071 | 200 |
| 66 | CariAct Q15 | 0.327 | 0.2231 | 0.2749 | 0.16 | 0.015 | 230 | 2.0 | 9400 | 145 | 32 | 0.351 | 997 | 245 |
| 67 | CariAct Q15 | 0.327 | 0.2231 | 0.2749 | 0.16 | 0.015 | 230 | 2.0 | 5400 | 145 | 32 | 0.446 | 622 | 204 |
| 68 | Aerolyst 3045 | 0.327 | 0.2231 | 0.2749 | 0.16 | 0.015 | 230 | 2.0 | 4500 | 145 | 32 | 0.475 | 787 | 205 |
| 69 | CariAct Q15 | 0.32669 | 0.28 | 0.345 | 0.033 | 0.015 | 220 | 2.0 | 3400 | 134 | 34 | 0.254 | 453 | 357 |
| 70 | CariAct Q15 | 0.327 | 0.28 | 0.345 | 0.033 | 0.015 | 220 | 2.0 | 13500 | 134 | 34 | 0.142 | 545 | 485 |
| 71 | CariAct Q15 | 0.327 | 0.28 | 0.345 | 0.033 | 0.015 | 220 | 2.0 | 7200 | 134 | 34 | 0.196 | 882 | 484 |
| 72 | Aerolyst 3045 | 0.327 | 0.25 | 0.375 | 0.033 | 0.015 | 220 | 2.0 | 4400 | 133 | 35 | 0.206 | 670 | 354 |
| 73 | CariAct Q15 | 0.327 | 0.25 | 0.375 | 0.033 | 0.015 | 220 | 2.0 | 3300 | 133 | 35 | 0.224 | 737 | 365 |
| 74 | G57 | 0.327 | 0.125 | 0.5 | 0.033 | 0.015 | 220 | 2.0 | 4200 | 129 | 38 | 0.104 | 1311 | 491 |
| 75* | CariAct Q15 | 0.327 | 0.025 | 0.6 | 0.033 | 0.015 | 220 | 2.0 | 4800 | 128 | 40 | 0.037 | 1217 | 1095 |
| 76* | Aerolyst 3045 | 0.327 | 0.025 | 0.6 | 0.033 | 0.015 | 220 | 2.0 | 4400 | 128 | 40 | 0.038 | 1282 | 1008 |
| 77 | G57 | 0.3261 | 0.2598 | 0.3191 | 0.08 | 0.015 | 230 | 2.0 | 4000 | 137 | 41 | 0.320 | 1220 | 293 |
| 78 | Aerolyst 3045 | 0.327 | 0.5 | 0.125 | 0.033 | 0.015 | 240 | 2.0 | 4500 | 147 | 41 | 0.505 | 1514 | 257 |
| 79 | G57 | 0.327 | 0.5 | 0.125 | 0.033 | 0.015 | 240 | 2.0 | 4000 | 147 | 41 | 0.524 | 1597 | 326 |
| 80 | CariAct Q15 | 0.327 | 0.5 | 0.125 | 0.033 | 0.015 | 240 | 2.0 | 3900 | 147 | 41 | 0.528 | 1546 | 229 |
| 81 | Aerolyst 3045 | 0.327 | 0.2231 | 0.2749 | 0.16 | 0.015 | 240 | 2.0 | 4500 | 145 | 43 | 0.469 | 1311 | 214 |
| 82 | G57 | 0.327 | 0.2231 | 0.2749 | 0.16 | 0.015 | 240 | 2.0 | 4000 | 145 | 43 | 0.487 | 1411 | 263 |
| 83 | Aerolyst 3045 | 0.327 | 0.2769 | 0.3411 | 0.04 | 0.015 | 230 | 2.0 | 21600 | 134 | 43 | 0.108 | 2079 | 518 |
| 84 | G57 | 0.327 | 0.2769 | 0.3411 | 0.04 | 0.015 | 230 | 2.0 | 4000 | 134 | 43 | 0.251 | 1348 | 402 |
| 85 | CariAct Q15 | 0.32669 | 0.28 | 0.345 | 0.033 | 0.015 | 230 | 2.0 | 3400 | 134 | 44 | 0.252 | 804 | 407 |
| 86 | CariAct Q15 | 0.327 | 0.28 | 0.345 | 0.033 | 0.015 | 230 | 2.0 | 9000 | 134 | 44 | 0.175 | 2374 | 561 |
| 87 | Aerolyst 3045 | 0.327 | 0.28 | 0.345 | 0.033 | 0.015 | 230 | 2.0 | 4500 | 134 | 44 | 0.232 | 1604 | 418 |
| 88 | G57 | 0.327 | 0.2948 | 0.3632 | 0 | 0.015 | 230 | 2.0 | 4000 | 132 | 45 | 0.189 | 1526 | 578 |
| 89 | CariAct Q15 | 0.327 | 0.28 | 0.345 | 0.033 | 0.015 | 220 | 1.7 | 5200 | 128 | 48 | 0.223 | 1354 | 405 |
| 90 | CariAct Q15 | 0.327 | 0.241 | 0.297 | 0.12 | 0.015 | 240 | 2.0 | 3300 | 140 | 48 | 0.417 | 1155 | 212 |

-continued

| Ex | Catalyst | N2 Feed (mol %) | EtOH Feed (mol %) | Ethoxyethane Feed (mol %) | Water Feed (mol %) | Methane Feed (mol %) | Reactor Temperature (° C.) | Pressure (MPa) | GHSV (h − 1) | Dew Point After Reaction to Equilibrium (° C.) | T reaction − T dew point − 40 × P total feed + 40 × P inerts | (P water/ (P ethanol + P ethoxyethane))/ (8 × 10 − 5 × GHSV + 0.75) | Ethene STY (g-l-hr) | Ethane in Ethene (ppm wt) |
|---|---|---|---|---|---|---|---|---|---|---|---|---|---|---|
| 91* | CariAct Q15 | 0.327 | 0.125 | 0.5 | 0.033 | 0.015 | 230 | 2.0 | 21600 | 129 | 48 | 0.045 | 1851 | 1257 |
| 92 | G57 | 0.327 | 0.125 | 0.5 | 0.033 | 0.015 | 230 | 2.0 | 15500 | 129 | 48 | 0.056 | 2663 | 1358 |
| 93* | CariAct Q15 | 0.327 | 0 | 0.608 | 0.05 | 0.015 | 230 | 2.0 | 5200 | 128 | 50 | 0.040 | 1594 | 1360 |
| 94* | Aerolyst 3045 | 0.327 | 0 | 0.608 | 0.05 | 0.015 | 230 | 2.0 | 4100 | 128 | 50 | 0.043 | 1548 | 1297 |
| 95 | CariAct Q15 | 0.327 | 0.375 | 0.25 | 0.033 | 0.015 | 240 | 2.0 | 5300 | 138 | 50 | 0.312 | 1888 | 279 |
| 96 | Aerolyst 3045 | 0.327 | 0.375 | 0.25 | 0.033 | 0.015 | 240 | 2.0 | 4500 | 138 | 50 | 0.330 | 1871 | 335 |
| 97* | G57 | 0.327 | 0 | 0.658 | 0 | 0.015 | 230 | 2.0 | 3900 | 127 | 50 | 0.000 | 2218 | 2157 |
| 98 | Aerolyst 3045 | 0.3261 | 0.2598 | 0.3191 | 0.08 | 0.015 | 240 | 2.0 | 4500 | 137 | 51 | 0.305 | 1752 | 292 |
| 99 | CariAct Q15 | 0.3261 | 0.2598 | 0.3191 | 0.08 | 0.015 | 240 | 2.0 | 4400 | 137 | 51 | 0.307 | 2008 | 375 |
| 100 | G57 | 0.3261 | 0.2598 | 0.3191 | 0.08 | 0.015 | 240 | 2.0 | 4000 | 137 | 51 | 0.316 | 1906 | 477 |
| 101 | CariAct Q15 | 0.32669 | 0.28 | 0.345 | 0.033 | 0.015 | 240 | 2.0 | 3300 | 134 | 54 | 0.249 | 1240 | 591 |
| 102 | G57 | 0.327 | 0.28 | 0.345 | 0.033 | 0.015 | 240 | 2.0 | 18100 | 134 | 54 | 0.115 | 3461 | 937 |
| 103 | Aerolyst 3045 | 0.327 | 0.28 | 0.345 | 0.033 | 0.015 | 240 | 2.0 | 15500 | 134 | 54 | 0.127 | 3429 | 911 |
| 104 | CariAct Q15 | 0.327 | 0.28 | 0.345 | 0.033 | 0.015 | 240 | 2.0 | 8700 | 134 | 54 | 0.174 | 3188 | 892 |
| 105 | Aerolyst 3045 | 0.327 | 0.28 | 0.345 | 0.033 | 0.015 | 240 | 2.0 | 4100 | 134 | 54 | 0.234 | 2423 | 533 |
| 106 | G57 | 0.327 | 0.28 | 0.345 | 0.033 | 0.015 | 240 | 2.0 | 3900 | 134 | 54 | 0.237 | 2333 | 605 |
| 107 | CariAct Q15 | 0.327 | 0.125 | 0.5 | 0.033 | 0.015 | 240 | 2.0 | 9400 | 129 | 58 | 0.073 | 4505 | 2094 |
| 108* | Aerolyst 3045 | 0.327 | 0 | 0.608 | 0.05 | 0.015 | 240 | 2.0 | 15500 | 128 | 60 | 0.023 | 3230 | 1982 |
| 109* | CariAct Q15 | 0.327 | 0.025 | 0.6 | 0.033 | 0.015 | 240 | 2.0 | 9400 | 128 | 60 | 0.027 | 5051 | 2080 |
| 110 | CariAct Q15 | 0.327 | 0.28 | 0.345 | 0.033 | 0.015 | 240 | 1.7 | 7200 | 128 | 68 | 0.190 | 2917 | 1083 |
| 111 | CariAct Q15 | 0.327 | 0.28 | 0.345 | 0.033 | 0.015 | 230 | 1.4 | 7200 | 121 | 72 | 0.195 | 2137 | 1129 |
| 112 | G57 | 0.327 | 0.28 | 0.345 | 0.033 | 0.015 | 230 | 1.4 | 4600 | 121 | 72 | 0.231 | 2370 | 854 |
| 113 | Aerolyst 3045 | 0.327 | 0.28 | 0.345 | 0.033 | 0.015 | 230 | 1.4 | 4500 | 121 | 72 | 0.233 | 1899 | 707 |
| 114 | CariAct Q15 | 0.327 | 0.28 | 0.345 | 0.033 | 0.015 | 230 | 1.4 | 3900 | 121 | 72 | 0.243 | 1921 | 707 |
| 115 | G57 | 0.327 | 0.28 | 0.345 | 0.033 | 0.015 | 210 | 1.0 | 18100 | 109 | 75 | 0.120 | 1124 | 1318 |
| 116* | G57 | 0.327 | 0.28 | 0.345 | 0.033 | 0.015 | 240 | 1.4 | 18100 | 121 | 82 | 0.115 | 4867 | 2162 |
| 117* | CariAct Q15 | 0.327 | 0.28 | 0.345 | 0.033 | 0.015 | 240 | 1.4 | 7200 | 121 | 82 | 0.191 | 3220 | 1322 |
| 118* | Aerolyst 3045 | 0.327 | 0.28 | 0.345 | 0.033 | 0.015 | 240 | 1.4 | 4500 | 121 | 82 | 0.228 | 2862 | 966 |
| 119* | CariAct Q15 | 0.327 | 0 | 0.608 | 0.05 | 0.015 | 210 | 1.0 | 4100 | 99 | 84 | 0.046 | 1144 | 5341 |
| 120* | Aerolyst 3045 | 0.327 | 0 | 0.608 | 0.05 | 0.015 | 210 | 1.0 | 4000 | 99 | 84 | 0.046 | 1010 | 5919 |
| 121* | G57 | 0.327 | 0.28 | 0.345 | 0.033 | 0.015 | 220 | 1.0 | 18100 | 109 | 84 | 0.120 | 2166 | 1837 |
| 122* | CariAct Q15 | 0.327 | 0.28 | 0.345 | 0.033 | 0.015 | 220 | 1.0 | 8700 | 109 | 84 | 0.182 | 2114 | 1646 |
| 123* | CariAct Q15 | 0.327 | 0.28 | 0.345 | 0.033 | 0.015 | 220 | 1.0 | 5200 | 109 | 84 | 0.226 | 1906 | 966 |
| 124* | G57 | 0.327 | 0 | 0.608 | 0.05 | 0.015 | 220 | 1.0 | 16700 | 100 | 94 | 0.023 | 2318 | 8235 |
| 125* | G57 | 0.327 | 0 | 0.608 | 0.05 | 0.015 | 220 | 1.0 | 3900 | 100 | 94 | 0.045 | 1868 | 4638 |
| 126* | G57 | 0.327 | 0.28 | 0.345 | 0.033 | 0.015 | 230 | 1.0 | 4600 | 109 | 94 | 0.231 | 2860 | 1023 |
| 127* | G57 | 0.327 | 0 | 0.608 | 0.05 | 0.015 | 230 | 1.0 | 16700 | 100 | 104 | 0.022 | 3450 | 8504 |
| 128* | Aerolyst 3045 | 0.327 | 0 | 0.608 | 0.05 | 0.015 | 230 | 1.0 | 4000 | 100 | 104 | 0.044 | 2206 | 6391 |
| 129* | G57 | 0.327 | 0 | 0.608 | 0.05 | 0.015 | 230 | 1.0 | 3900 | 100 | 104 | 0.044 | 2513 | 5576 |
| 130* | G57 | 0.327 | 0.28 | 0.345 | 0.033 | 0.015 | 240 | 1.0 | 18100 | 109 | 104 | 0.115 | 5881 | 2460 |
| 131* | CariAct Q15 | 0.327 | 0.28 | 0.345 | 0.033 | 0.015 | 240 | 1.0 | 8700 | 109 | 104 | 0.175 | 4747 | 1899 |
| 132* | G57 | 0.327 | 0.28 | 0.345 | 0.033 | 0.015 | 240 | 1.0 | 4600 | 109 | 104 | 0.226 | 4072 | 1261 |

| Ex | Catalyst | N2 Feed (mol %) | EtOH Feed (mol %) | Ethoxyethane Feed (mol %) | Water Feed (mol %) | Methane Feed (mol %) | Reactor Temperature (°C.) | Pressure (MPa) | GHSV (h-1) | Dew Point After Reaction to Equilibrium (°C.) | T reaction – T dew point – 40 × P total feed + 40 × P inerts | (P water/(P ethanol + P ethoxyethane))/(8 × 10 – 5 × GHSV + 0.75) | Ethene STY (g-l-hr) | Ethane in Ethene (ppm wt) |
|---|---|---|---|---|---|---|---|---|---|---|---|---|---|---|
| 133* | Aerolyst 3045 | 0.327 | 0.28 | 0.345 | 0.033 | 0.015 | 240 | 1.0 | 4500 | 109 | 104 | 0.228 | 3338 | 1144 |
| 134* | CariAct Q15 | 0.327 | 0.28 | 0.345 | 0.033 | 0.015 | 240 | 1.0 | 3200 | 109 | 104 | 0.252 | 2490 | 1039 |
| 135* | CariAct Q15 | 0.327 | 0 | 0.608 | 0.05 | 0.015 | 240 | 1.0 | 15500 | 100 | 114 | 0.023 | 3663 | 6779 |
| 136* | CariAct Q15 | 0.327 | 0 | 0.608 | 0.05 | 0.015 | 240 | 1.0 | 5300 | 100 | 114 | 0.039 | 3181 | 7257 |
| 137* | CariAct Q15 | 0.327 | 0 | 0.608 | 0.05 | 0.015 | 240 | 1.0 | 5300 | 100 | 114 | 0.039 | 3565 | 7028 |

*indicates a comparative example

The invention claimed is:

1. A process for the production of ethene by the vapour phased chemical dehydration of a feed comprising ethanol, water and ethoxyethane in a reactor at elevated temperature and pressure in the presence of a bed of catalyst comprising a supported heteropolytungstic acid said process comprising maintaining or configuring the reactor so that it operates in a regime which satisfies the following parameters:

$$0.05 < (P_{water}/(P_{ethanol}+P_{ethoxyethane}))/(8 \times 10^{-5} \times GHSV+0.75) \quad (1)$$

and $$-20 < T_{reaction} - T_{dew\ point} - 40 \times P_{total\ feed} + 40 \times P_{inerts} < +80 \quad (2)$$

wherein $P_{water}$, $P_{ethanol}$ and $P_{ethoxyethane}$ are respectively the partial pressures of water, ethanol and ethoxyethane in the thermodynamic equilibrium composition of the feed at the operating temperature and pressure of the process (in MPa), GHSV is the gas hourly space velocity of feed over the catalyst in hr$^{-1}$, T reaction is the temperature of reaction in ° C., $T_{dew\ point}$ is the dew point temperature of the feed at its thermodynamic equilibrium composition in ° C., $P_{total\ feed}$ is the total pressure of feed (in MPa) and $P_{inerts}$ is the partial pressure of inerts in the feed (in MPa).

2. A process as claimed in claim 1 wherein:

$$0.1 < (P_{water}/(P_{ethanol}+P_{ethoxyethane}))/(8 \times 10^{-5} \times GHSV+0.75).$$

3. A process as claimed in claim 2 wherein:

$$0.2 < (P_{water}/(P_{ethanol}+P_{ethoxyethane}))/(8 \times 10^{-5} \times GHSV+0.75).$$

4. A process as claimed in claim 3 wherein:

$$0.3 < (P_{water}/(P_{ethanol}+P_{ethoxyethane}))/(8 \times 10^{-5} \times GHSV+0.75).$$

5. A process as claimed in claim 1 wherein:

$$-20 < T_{reaction} - T_{dew\ point} - 40 \times P_{total\ feed} + 40 \times P_{inerts} < 60.$$

6. A process as claimed in claim 5 wherein:

$$0 < T_{reaction} - T_{dew\ point} - 40 \times P_{total\ feed} + 40 \times P_{inerts} < 50.$$

7. A process as claimed in claim 6 wherein:

$$20 < T_{reaction} - T_{dew\ point} - 40 \times P_{total\ feed} + 40 \times P_{inerts} < 40.$$

8. A process as claimed in claim 1 wherein the feed contains an inert, non-condensable diluent selected from 2-methylpropane, n-butane and ethene.

9. A process as claimed in claim 1 wherein the vapour phase chemical dehydration is effected in a series of two or more reactors operated adiabatically in which conversion of the feed is progressive and each subsequent reactor is operated at a higher temperature than its predecessor.

10. A process as claimed in claim 8, wherein the diluent is introduced at a plurality of points in the catalyst bed and/or the reactors.

11. A process as claimed in claim 1 wherein the supported heteropolytungstic acid catalyst is one having the following characteristic:

PV > 0.6 − 0.3 × [HPA loading/Surface Area of Catalyst]

wherein PV is the pore volume of the dried supported heteropolytungstic acid catalyst (measured in ml/g catalyst); HPA loading is the amount of heteropolyacid present in the dried supported heteropolyacid catalyst (measured in micro moles per gram of catalyst) and Surface Area of Catalyst is the surface area of the dried supported heteropolytungstic acid catalyst (measured in m$^2$ per gram of catalyst).

12. A process as claimed in claim 8 wherein the equilibrium feed composition contains more than 15% by volume water.

13. A process as claimed in claim 8 wherein the ethene produced contains less than 10 ppm of oxygen containing compounds.

* * * * *